(12) United States Patent
Alie et al.

(10) Patent No.: US 10,446,132 B2
(45) Date of Patent: Oct. 15, 2019

(54) ACOUSTIC LENS AND APPLICATIONS THEREOF

(71) Applicant: Butterfly Network, Inc., Guilford, CT (US)

(72) Inventors: Susan A. Alie, Stoneham, MA (US); Jaime Scott Zahorian, Guilford, CT (US); Christopher Thomas McNulty, Guilford, CT (US); Paul Francis Cristman, New Haven, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/271,658

(22) Filed: Feb. 8, 2019

(65) Prior Publication Data
US 2019/0180728 A1 Jun. 13, 2019

Related U.S. Application Data

(63) Continuation of application No. PCT/US2017/066124, filed on Dec. 13, 2017.
(Continued)

(51) Int. Cl.
| | |
|---|---|
| *G10K 11/02* | (2006.01) |
| *G10K 11/165* | (2006.01) |
| *G10K 11/168* | (2006.01) |
| *G10K 11/30* | (2006.01) |
| *A61B 8/00* | (2006.01) |

(Continued)

(52) U.S. Cl.
CPC ............... *G10K 11/02* (2013.01); *A61B 8/00* (2013.01); *A61B 8/4444* (2013.01); *A61B 8/546* (2013.01); *B06B 1/0292* (2013.01); *G10K 11/165* (2013.01); *G10K 11/168* (2013.01); *G10K 11/30* (2013.01); *A61B 8/08* (2013.01);
(Continued)

(58) Field of Classification Search
CPC ...... G10K 11/02; G10K 11/30; G10K 11/168; G10K 11/165; B06B 1/0292; A61B 8/546; A61B 8/4444; A61B 8/00; A61B 8/488; A61B 8/4483; A61B 8/4455; A61B 8/08; A61B 8/4411
See application file for complete search history.

(56) References Cited

U.S. PATENT DOCUMENTS

| 6,183,578 B1 * | 2/2001 | Ritter | ................... B06B 1/0611 156/155 |
| 9,067,779 B1 * | 6/2015 | Rothberg | ............ B81C 1/00238 |

(Continued)

OTHER PUBLICATIONS

International Search Report and Written Opinion dated Feb. 21, 2018 in connection with International Application No. PCT/US2017/066124.
(Continued)

*Primary Examiner* — Daniel Pihulic
(74) *Attorney, Agent, or Firm* — Wolf, Greenfield & Sacks, P.C.

(57) ABSTRACT

The disclosed embodiments relate to a portable ultrasound device. Specifically, the disclosed embodiments relate to an acoustic lens positioned at an ultrasound probe. The acoustic lens may be configured for impedance matching and signal attenuation. In one embodiment, ultrasound signal attenuation is provided by forming an acoustic lens as a solid admixture of signal attenuating particles in a polymer matrix.

21 Claims, 7 Drawing Sheets

Related U.S. Application Data

(60) Provisional application No. 62/433,275, filed on Dec. 13, 2016.

(51) Int. Cl.
  *B06B 1/02* (2006.01)
  *A61B 8/08* (2006.01)

(52) U.S. Cl.
  CPC .......... *A61B 8/4411* (2013.01); *A61B 8/4455* (2013.01); *A61B 8/4483* (2013.01); *A61B 8/488* (2013.01)

(56) References Cited

U.S. PATENT DOCUMENTS

| | | | | |
|---|---|---|---|---|
| 9,521,991 B2* | 12/2016 | Rothberg | ............... | A61B 8/145 |
| 9,592,030 B2* | 3/2017 | Rothberg | ............ | G01S 7/52084 |
| 2005/0075572 A1* | 4/2005 | Mills | .................... | B06B 1/0292 |
| | | | | 600/459 |
| 2005/0165312 A1* | 7/2005 | Knowles | ................ | G10K 11/02 |
| | | | | 600/459 |
| 2008/0156577 A1* | 7/2008 | Dietz | .................... | G10K 11/30 |
| | | | | 181/176 |
| 2008/0195003 A1* | 8/2008 | Sliwa | ...................... | A61N 7/02 |
| | | | | 601/3 |
| 2011/0055447 A1* | 3/2011 | Costa | .................... | G06F 1/1632 |
| | | | | 710/304 |
| 2011/0112406 A1* | 5/2011 | Rubinsztajn | ............ | C08L 83/04 |
| | | | | 600/459 |
| 2011/0114303 A1* | 5/2011 | Rhim | ...................... | A61B 8/00 |
| | | | | 165/185 |
| 2016/0007961 A1* | 1/2016 | Lee | ...................... | A61B 8/4494 |
| | | | | 600/459 |
| 2016/0203809 A1* | 7/2016 | Brock-Fisher | ........ | B06B 1/0292 |
| | | | | 600/459 |
| 2019/0180728 A1* | 6/2019 | Alie | ......................... | A61B 8/00 |

OTHER PUBLICATIONS

International Preliminary Report on Patentability dated Jun. 27, 2019 in connection with International Application No. PCT/US2017/066124.

* cited by examiner

| Manufacturer | EpoxySet | EpoxySet | DOW | DOW | DOW | DOW | Momentive | Wacker | DOW | |
|---|---|---|---|---|---|---|---|---|---|---|
| Product | LACE-31 | LACE-32 | Sylgard 160 | Sylgard 184 | CS-530 | MDX4-4210 | Silopren 2640 | Silpuran 6740/40 | OP1-20 | 630 RTV |
| Mix Ratio by weight (A:B) | 100/40 | 100/40 | 1:1 | 10:1 | 1:1 | 10:1 | 1:1 | 1:1 | 1:1 | 1:1 |
| Mixed Liquid Density gm/cm³ | 1.04 | 1.04 | 1.38 | 1.04 | 1.13 | 1.11 w/Catalyst | 1.12 | | | |
| Work life @ 25°C | 30-60 mins | 30-60 mins | 20 mins | 1.5 hrs | | | 3 days in machine | | | |
| Cure Schedule | 6-8hrs @65C | 6-8hrs @65C | 4 min @100C | .58hrs @100C | 0-8hrs @177C | 2hrs @65C | 4hrs @200C | | 2hr @150C | |
| Hardness (Shore A) | 30-32 | 30-32 | 56 | 43 | 30-33 | 30 | 42 | 38 | 22 | |
| Specific Gravity (Cured Sample) | 1.05 | 1.06 | 1.37 | 1.03 | | 1.1 | 1.12 | 1.1 | 1.12 | |
| Velocity (Longitudinal), m/sec | 1449 | 1439 | 950 | 1027 | | | | | 975 | |
| Acoustic Impedance Z (Longitudinal), Mrayl | 1.52 | 1.45 | 1.5 | 1.04 | | | | | 1.03 @4Mhz | |
| Attenuation coefficient @ 3 MHz | 0.37 | 0.39 | 0.4 | | | | | | .75 Np/cm @4Mhz | |
| Attenuation coefficient @ 5 MHz | 0.65 | 0.79 | | | | | | | | |
| Attenuation coefficient @ 7 MHz | 1.17 | 1.39 | | | | | | | | |
| Attenuation coefficient @ 10 MHz | 2.33 | 2.68 | | | | | | | | |
| Thermal Conductivity btu/hr ft degF | | | 0.36 | 0.15 | | | | | | |
| Thermal Conductivity Watts/m degK | | | 0.62 | 0.27 | | | | | | |
| Tensile Strength psi | | | 535 | 980 | 190-1310 | 730 | 1160 | 1262 | 935 | |
| Elongation % | | | 75-105 | 120 | 793-833 | 470 | 600 | 710 | 690 | |
| Resistivity ohm-cm | | | 5.60E+14 | 2.90E+14 | | 2.00E+15 | | | | |
| Dielectric Strength volts/mil | | | 475 | 500 | | 575 | | | | |
| Material | Polyurethane | Polyurethane | Silicone Elastomer | Polydimethylsiloxane (Silicone Elastomer) | LSR | Silicone Elastomer | LSR | LSR | LSR | |
| Tear Strength kN/m | | | 2.1 | 0.2 | 27 | | 40 | 30 | 21.9 | |
| BioMedical Grade | | | | | Yes | Yes | Yes | Yes | Yes | |
| Young's Modulus(Generally) 3 to 30 for silicone rubber | | | | | | <2Mpa | | | | |
| Poisson's ratio(Generally 0.47 to 0.49 for silicone rubber | | | | | | | | | | |
| Desire Material viscoelasticity with a glass-transition (Tg) temperature lower than room temperature | | | | | | | | | | |

FIG. 2

ACOUSTIC LENS AND APPLICATIONS THEREOF

CROSS-REFERENCE TO RELATED APPLICATIONS

The present application is a Continuation claiming the benefit of Patent Application Serial No. PCT/US2017/066124, filed Dec. 13, 2017, entitled "ACOUSTIC LENS AND APPLICATIONS THEREOF," which is hereby incorporated herein by reference in its entirety.

Patent Application Serial No. PCT/US2017/066124 claims the benefit of U.S. provisional Application Ser. No. 62/433,275, filed Dec. 13, 2016 under and entitled "ACOUSTIC LENS FOR ULTRASOUND DEVICE AND RELATED APPARATUS AND METHODS," which is hereby incorporated herein by reference in its entirety.

FIELD

The disclosure relates to an ultrasound probe having an acoustic lens configured for impedance matching and signal attenuation. In an exemplary embodiment, the disclosure relates to using an RTV material, optionally with particles, to decrease or increase ultrasound attenuation. In another exemplary embodiment, a low attenuating layer of polyether block amide may be used as standoff to the lens. The lens may be configured with an ergonomic shape. In still another embodiment, we use a layer with specific acoustic properties to reduce acoustic cross talk. The layer may comprise RTV material and Aluminum oxide or graphite. An acoustic layer backing may also be used. The acoustic layer backing may comprise tungsten epoxy mix. The acoustic layer backing is configured to match the impedance of the transducer while being highly attenuating.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

With respect to treatment, as an alternative to more invasive types of surgical procedures, many physicians are employing the use of high intensity focused ultrasound (HIFU) as a technique to therapeutically treat internal body tissues. With HIFU, an ultrasound signal of sufficient power (e.g., pressure and velocity) and time is focused on a target volume of tissue in order to change a state of the tissue by rapid heating and/or mechanical destruction by cavitation. The treated tissue may form one or more lesions that may be left in the body and thereafter absorbed through normal physiological processes.

In order to effectively treat tissue, the energy of the delivered HIFU signal must be sufficient to cause the desired physical effect(s). On the other hand, the delivered energy should not be too large or uncontrolled so as to cause unintended collateral damage to healthy tissues surrounding the target volume. The non-homogenous nature of tissue(s) in the body creates variations in attenuation, propagation velocity, and acoustic impedance that modify the expected acoustic wave propagation and deposition of HIFU energy delivered to a target tissue volume when compared to homogeneous material. Thus, certain treatment regimens that are solely based on applying a predetermined dose of HIFU energy may therefore achieve inconsistent results due to such variations.

BRIEF DESCRIPTION OF THE DRAWINGS

Various aspects and embodiments of the disclosed technology will be described with reference to the following Figures. It should be appreciated that the figures are not necessarily drawn to scale. Items appearing in multiple figures are indicated by the same reference number in all the figures in which they appear.

FIG. 2 illustrates a table of materials for an exemplary acoustic lens composition according to one embodiment of the disclosure;

DETAILED DESCRIPTION

The efficiency of ultrasound probes used in medical applications to obtain cross-sectional images of various parts of a human body is hampered by acoustic reflections occurring at the interface between the probe and the patient. Acoustic reflections are caused by acoustic impedance mismatching between the probe and the surface of the body of the patient. This may be particularly problematic when there is a gap between the probe and the probed surface.

Moreover, applicant has appreciated that the lifetime of ultrasonic transducers in an ultrasound probe may be reduced by mechanical stress. The mechanical stress may cause deformations of the transducer, which, in turn, may lead to a degradation of the transducer's performance.

Therefore, aspects of the present application provide an acoustic lens that minimizes acoustic reflections by providing impedance matching between the probe and the probed surface. In some embodiments, the acoustic lens also alters the acoustic wave-fronts to provide acoustic focusing. In some embodiments, the acoustic lens may have a low elastic modulus. In some embodiments, the acoustic lens is electrically insulating. In some embodiments, the acoustic lens attenuates surface waves along a surface of the acoustic transducers, without attenuating the desired ultrasound waves transmitted to and/or received from a subject. The attenuation behavior may be facilitated by suitable choice of the material of the acoustic lens.

According to aspects of the present application, an acoustic lens may be fabricated using a material that provides acoustic impedance matching and exhibits a low elastic modulus, low acoustic attenuation and high electric resistivity. Further, the acoustic lens may be molded into shapes and dimensions that increase, and in some embodiments, optimize, the capability to focus acoustic waves to targets having sizes approximately equal to the acoustic wavelength.

The aspects and embodiments described above, as well as additional aspects and embodiments, are described further below. These aspects and/or embodiments may be used individually, all together, or in any combination of two or more, as the application is not limited in this respect.

Figure 1:
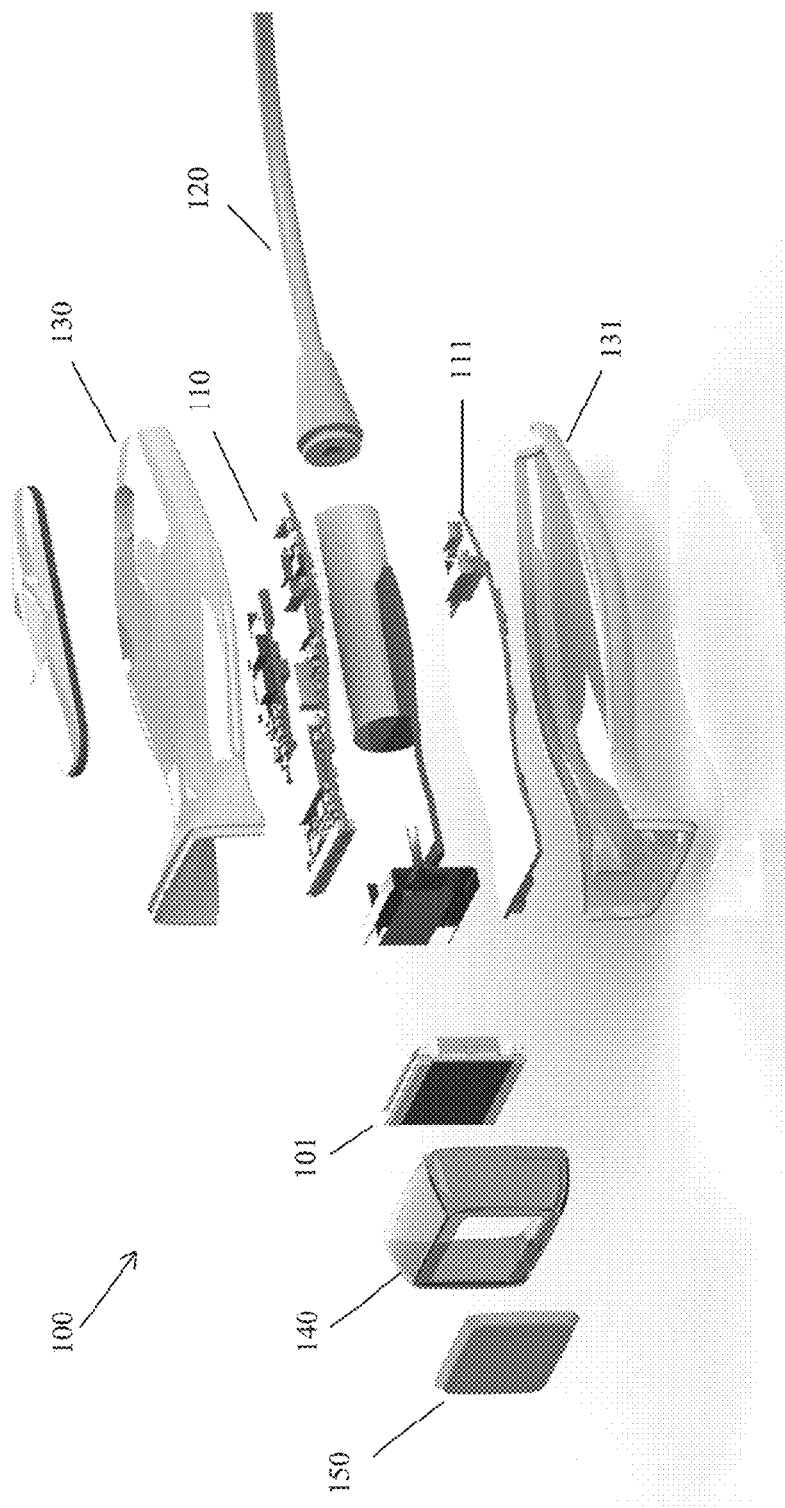
FIG. 1 is an exploded view of an ultrasound probe including an acoustic lens according to an embodiment of the disclosure.

As described, aspects of the present application relate to acoustic lenses for an ultrasound probe. FIG. 1 is an exploded view of an ultrasound probe 100, comprising an ultrasonic transducer arrangement 101, a first circuit board 110, a second circuit board 111, a cable 120 and an acoustic lens 150. Ultrasound probe 100 may be encapsulated with a chassis, having an upper case 130 and a lower case 131 and may further comprise a protective element 140 to protect the interface between the ultrasonic transducer arrangement 101 and the patient (not shown in FIG. 1).

Ultrasonic transducer arrangement 101 may comprise one or more ultrasonic transducers in any suitable arrangement, such as an array. The individual ultrasonic transducers of ultrasonic transducer arrangement 101 may be capacitive micromachined ultrasonic transducers (CMUTs), piezoelectric micromachined ultrasonic transducers (PMUTs), or other suitable types of ultrasonic transducers. Circuit boards 110 and 111 may comprise circuitry to operate the ultrasonic transducer arrangement 101 in transmit mode, to transmit ultrasound signals, or receive mode, to convert received ultrasound signals into electrical signals. The circuitry may power the ultrasonic transducer arrangement 101, generate drive signals for the ultrasonic transducer arrangement 101, process electrical signals produced by the ultrasonic transducer arrangement 101, or perform any combination of such functions. Cable 120 may carry any suitable analog and/or digital signal to/from circuit boards 110 and 111.

According to aspects of the present application, acoustic lens 150 may be configured to focus acoustic energy to spots having areas of the size required for high-intensity focused ultrasound (HIFU) procedures. Furthermore, acoustic lens 150 may acoustically couple ultrasonic transducer arrangement 101 to the patient to minimize acoustic reflections and attenuation. In some embodiments, acoustic lens 150 may be fabricated with materials providing impedance matching between ultrasonic transducer arrangement 101 and the patient.

According to aspects of the present application, acoustic lens 150 may be made of any combination of the materials listed in table 200 shown in FIG. 2. Table 200 presents nine materials, and for each material the following properties are presented: manufacturer, product, mix ratio by weight, mixed liquid density, work life, cure schedule, hardness, specific gravity, acoustic velocity, longitudinal acoustic impedance, acoustic attenuation coefficient at 3 MHz, 5 MHz, 7 MHz and 10 MHz, thermal conductivity, tensile strength, elongation, electric resistivity, dielectric strength, tear strength, biomedical grade, Young's modulus (elastic modulus) and Poisson's ratio.

In some embodiments, acoustic lens 150 may provide electric insulation and may comprise shielding to prevent electromagnetic interference (EMI). In other embodiments, EMI shielding layers may be added as a part of the process steps to fabricate wafers comprising one or more transducers of the type described herein.

In some embodiments, protective element 140 and acoustic lens 150 may provide a protective interface to absorb or reject stress between ultrasonic transducer arrangement 101 and the acoustic lens 150.

In some embodiments, the ultrasound probe 100 described herein may be used for diagnostic sonography to see internal body parts such as tendons, muscles, vessels, joints and internal organs. Acoustic probe 100 may also be used for obstetric ultrasound. In other embodiments, ultrasound probe 100 may be employed to detect motion by measuring Doppler effect. In yet other embodiments, ultrasound probe 100 may be employed in high-intensity focused ultrasound techniques.

Figure 3:
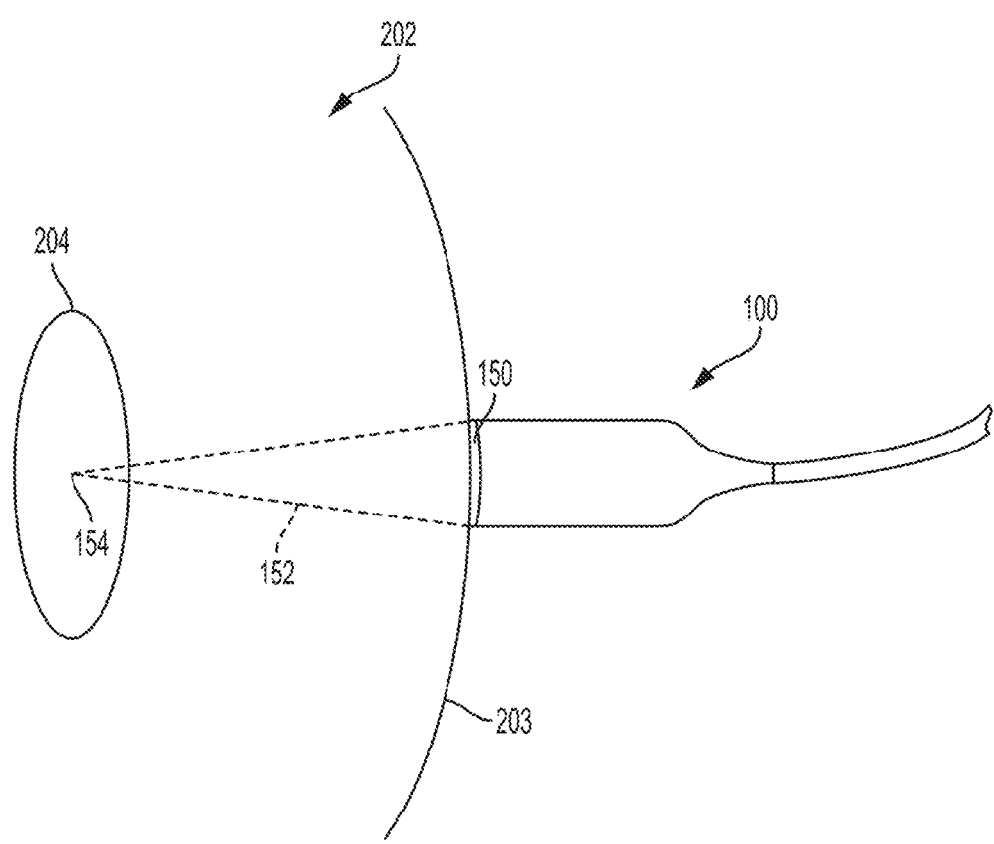
FIG. 3 illustrates ultrasound probe 100 of FIG. 1 as used on a patient.

FIG. 3 illustrates ultrasound probe 100 while being used on patient 202, according to aspect of the present application. In the non-limiting embodiment of FIG. 3, ultrasound probe 100 may be disposed such that acoustic lens 150 is in contact with a surface 203 of the body of patient 202. According to aspects of the present application, acoustic lens 150 may acoustically couple ultrasound probe 100 to patient 202 so as to minimize acoustic reflections.

In the non-limiting embodiment, ultrasound probe 100 may be configured to focus acoustic energy on a spot 154 of an organ 204 of patient 202. Acoustic lens 150 may shape the wave-fronts of the emitted acoustic wave to produce longitudinal profile 152, as illustrated in FIG. 3.

Figure 4:
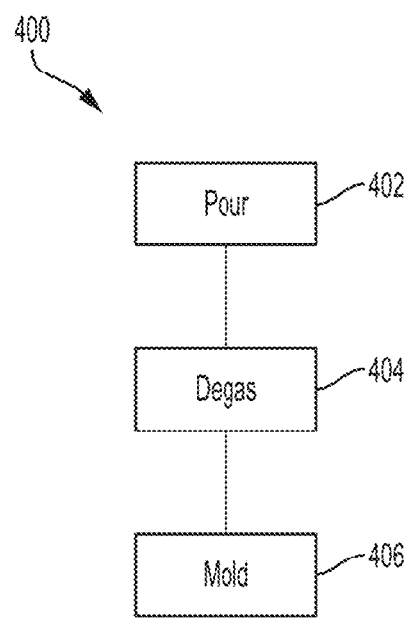
FIG. 4 is a flowchart of an exemplary method to fabricate an ultrasound probe acoustic lens according to an embodiment of the disclosure.

FIG. 4 illustrates the steps of a method 400 to fabricate acoustic lens 150, according to aspects of the present application. In step 402, any suitable combination of materials shown in table 200 above may be poured into a cast, having a desired shape and dimension. In step 404, the cast may be placed in a chamber and the chamber may be degassed. In step 406, the cast may be taken out of the degas chamber, and acoustic lens 150 may be molded to the desired shape and dimension.

In some embodiments, acoustic lens 150 may be fabricated as a stand-alone piece separate from the ultrasound probe. In other embodiments, acoustic lens 150 may be molded on the ultrasonic transducer arrangement or on the ultrasound probe. In still another embodiment, acoustic lens is formed in liquid state and degassed. The array is then installed on the mold and the mold is allowed to cure.

In some embodiments, acoustic lens 150 may be adhered to a chip on which the ultrasonic transducers are formed or to the probe using a bubble-free layer of unsolidified material as a glue layer. The material may be selected from any material shown in table 200, and in some embodiments, may be the same material as the acoustic lens.

Ultrasound probes using acoustic lenses of the types described herein may experience significantly improved efficiency compared to probes lacking such lenses. Acoustic reflections occurring at the interface between the patient and the ultrasonic transducer arrangement may cause a significant decrease in the ability of an ultrasound probe to generate data adequate for meaningful images or to effectively heal damaged tissues. In some embodiments, utilizing an acoustic lens of the types described herein may provide a substantial efficiency increase by providing acoustic impedance matching at the interface between the patient and the transducer. The efficiency may be represented by the ratio of the acoustic power hitting the target to the total power transmitted by the transducer.

In addition, the increase in the ability to focus acoustic energy on targeted tissues or organs may be significant. In some embodiments, utilizing an acoustic lens of the types described herein may provide a substantial improvement in the focusing resolution, measured as the minimum area that can be hit by an acoustic wave.

Figure 5:
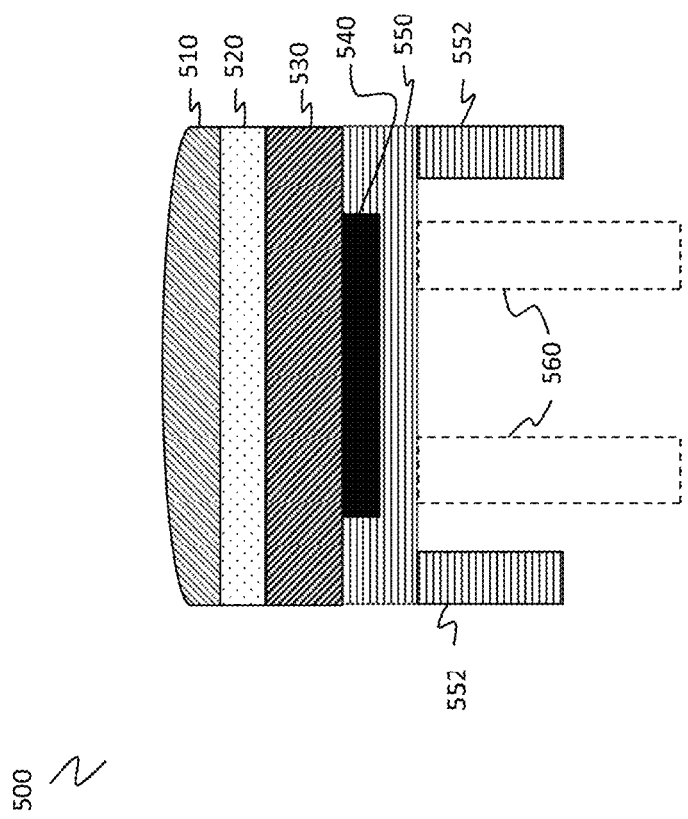
FIG. 5 is a first illustrative example of an ultrasound probe structure according to certain embodiments of the disclosure.

FIG. 5 is a first illustrative example of an ultrasound structure according to certain embodiments of the disclosure. The probe structure 500 includes acoustic lens includes acoustic lens outer surface 510, acoustic lens inner surface 520 and transducer array 530. The transducer array may be placed over epoxy layer 540 and heat sink 550.

Acoustic lens outer surface 510 may comprise semi-composite lens material. For example, outer surface 510 may comprise one or more room-temperature vulcanizing (RTV) compound. An exemplary RTV material or compound is Momentive RTV 630® (Momentive Performance Materials Inc., Waterford, N.Y.) silicon rubber compound. Acoustic outer layer surface 510 may also comprise any material (or mixture of material) configured for attenuation and impedance matching of ultrasound harmonic waves. In an exemplary embodiment, acoustic outer surface 510 may comprise a thin layer configured to attenuate ultrasound harmonics. In certain applications, layer 510 may be shaped for ergonomic application. That is, it may be shaped to fit between ribs of a subject's rib cage or contoured to accommodate ultrasound maneuvering and positioning. The acoustic lens outer surface 510 may be optionally configured to receive a gel pad (not shown). In such embodiments, outer surface 510 may have one or more retaining prongs (not shown) to receive and maintain a gel pad adjacent acoustic lens surface 510. The gel pad may be discarded after each use.

Acoustic lens inner surface 520 may optionally be interposed between outer surface 510 and the transducer array. Acoustic lens inner surface 520 may be used to reduce surface acoustic cross talk. The inner surface 520 may comprise one or more particles for absorbing or scattering sound waves that are generating by transducer array 530 or are directed back to the transducer array (e.g., the returning ultrasound waves). In some embodiment, inner surface 520 provides a damping effect for the ultrasound waves. In one embodiment, inner surface 520 may comprise solid particles dispersed in a solid medium. The particles may be configured to absorb or attenuate sound waves. Exemplary particles may comprise one or more thermoplastic elastomers such as polyether block amide, for example, PEBAX® (Arkema, Clear Lake, Tex.). PEBAX may be used as a lower loss material to avoid attenuating the ultrasound. PEBAX may also be used to act as a standoff layer. A standoff layer may be configured to make up the difference in layer height. In certain embodiments, it may be desired to have a layer on a non-attenuating material before the lens in order to not decimate the signal. In such embodiments, PEBAX may be used as a lower loss material to avoid attenuating the ultrasound. In another embodiment, inner surface layer 520 may define an attenuating layer comprising RTV material and $Al_2O_3$, or RTV material and graphite, or RTV material and PEBAX or combinations thereof.

In another embodiment, the particles may comprise a thermoplastic elastomer or block co-polymer. In certain embodiments, the particles may be powder particles dispersed in a solid medium. In one embodiment, the average particles may be 10-100 microns or greater in size. In another embodiment, the average powder particles may be 100 microns or less in size. An exemplary PEBAX is RTV 615. The solid medium for dispersing PEBAX may comprise graphite or one or more fillers such as $Al_2O_3$. The aluminum oxide particles may be in the range of about 1-100 microns.

In an exemplary embodiment, inner surface 520 is formed as follows. First, a powder plastic composition of PEBAX is formed. The particles size can be about 100 microns or smaller. In some embodiments, the particles can be in the nanometer range. Next, the PEBAX particles then mixed with the RTV polymer which may be high-viscosity liquid. Filler material discussed above (e.g., $Al_2O_3$) may be also be used in the admixture. In certain embodiments, graphite may be used as the filler. The admixture may optionally be vacuumed to remove air or other gases. The admixture may be applied to transducer array surface 530 and allowed to cure. Alternatively, the admixture may be formed in a mold and applied to the array surface 530.

Transducer array 530 may comprise an array of ultrasound transducers in which a plurality of transducers is positioned in rows and columns to form the array. Each transducer may be defined by or comprise a capacitive micromachined ultrasonic transducer (CMUT). Each CMUT may have a membrane responsive to an applied electromagnetic force that causes vibration of the membrane to form an ultrasound waveform. The ultrasound waveform may be directed to a patient's body positioned adjacent the ultrasound device. Further, each CMUT may be configured to receive an ultrasound response from the patient's and process the ultrasound response to a corresponding ultrasound image. While not shown, the ultrasound probe structure 500 may further comprise circuitry to generate waveform(s) and to process ultrasound (acoustic) signals to digital signals. In addition, the probe may comprise power unit, such as battery or capacitor (not shown) for charging and operating the probe.

Referring again to FIG. 5, transducer array 530 is positioned over epoxy layer 540. Epoxy layer 540 may comprise one or more epoxy polymers configured to dampen and/or absorb acoustic energy 530. In certain embodiments, epoxy layer 540 may be a tungsten-epoxy layer. The epoxy layer may be integrated into heat sink 550 or it may be interposed between the heat sink and transducer array 530. In one embodiment, the epoxy layer comprises a mixture of EpoTek 353ND® (Epoxy Technology, Inc., Billerica, Mass.) and Tungsten particles ranging in size from 1 to 100 microns. This mixture may be configured to be matching to the acoustic properties of Si and may be thermally conductive.

Heat sink 550 is positioned below transducer array 530 to remove heat away from the transducers. The heat sink may optionally include tables 552. Tabs 552 may be configured to integrate ultrasound structure 500 into a housing (not shown). An exemplary heat sink may comprise copper, copper alloys or the like.

Circuit boards 560 may be optionally positioned between heat sink tabs 552. Circuit boards may include circuitry configured to process digital signals. Circuit boards 560 may also be responsible for power management and control. Each circuit board may comprise processing circuitry and memory configured to execute programmed signal processing steps. The processing steps may, for example, instruct each CMUT independently, as subgroups or a as a group. The CMUT may instruct the transducers to generate ultrasound signal(s) of desired wavelength to penetrate a proximal body at a desired depth. The processing steps may also communicate with each CMUT to receive ultrasound signal emitted from the body and convert the received ultrasound signal to digital information. Thus, circuit boards 560 may receive digital signals representative of the desired ultrasound signal and cause the transducer array to convert the digital signal to ultrasound signal for transmission into an adjacent body. It should note noted that while FIG. 5 shows two circuit boards 560, that the number of circuit boards and their positioning is entirely optional.

Figure 6:
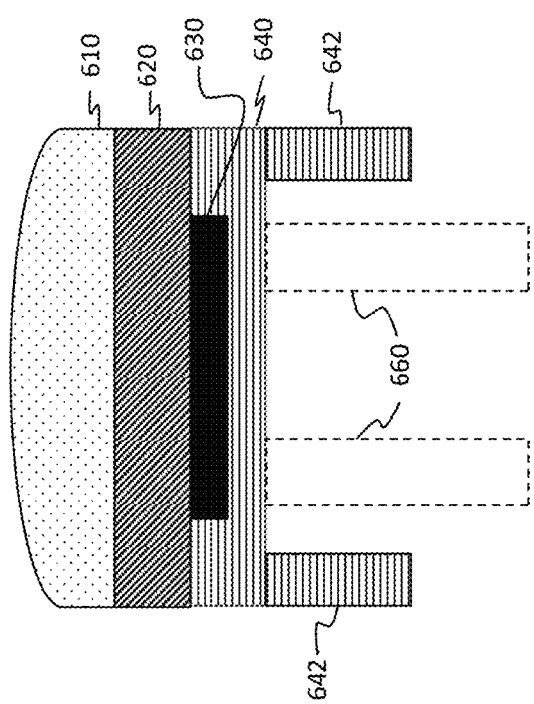
FIG. 6 is a second illustrative example of example of an ultrasound structure according to certain embodiments of the disclosure.

FIG. 6 is a second illustrative example of an ultrasound structure according to certain embodiments of the disclosure. The ultrasound structure 600 includes acoustic lens 610, transducer array 620, epoxy layer 630 and heat sink 640. FIG. 6 also shows optional heat sink tabs 642. Acoustic lens 610 may comprise a solid admixture of two or more material. For example, acoustic lens 610 may comprised of PEBAX in an RTV polymer. The particles may serve to reduce (or increase) the attenuation in the ultrasound signals. Additional material such as fillers or resin may also be included in the admixture. Fillers may comprise aluminum oxide or graphite if attenuation is desired.

Acoustic lens 610 may be positioned over transducer array 620. As discussed, transducer array 620 may comprise a plurality of transducers arranged in rows and columns. Epoxy layer 630 may be interposed between transducer array 620 and heat sink 640. In the embodiment of FIG. 6, epoxy layer 630 is embedded in heat sink 640. In another exemplary embodiment (not shown), epoxy layer 630 interfaces the entirety of a surface of transducer array 620. Heat sink 640 may comprise copper, copper alloys or the like. Optional copper tabs 642 may be included to extent heat dissipation from heat sink 640.

Optional circuit board 660 are illustrated in FIG. 6. Circuit boards 660 may be similar to those described at FIG. 5 and carryout functions including digital signal processing and power management/control.

Figure 7:
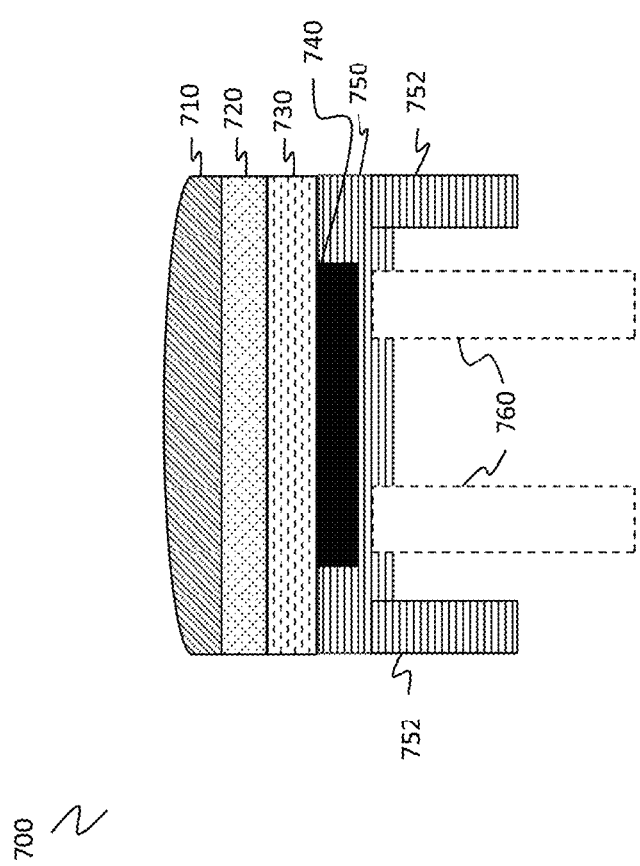
FIG. 7 illustrates a third exemplary embodiment of an ultrasound structure according to certain embodiments of the disclosure.

FIG. 7 illustrates a third exemplary embodiment of an ultrasound structure according to certain embodiments of the disclosure. In FIG. 7, the ultrasound structure 700 comprise an acoustic lens with three sublayers layers 710, 720 and 730. Layer 710 is the body contact layer and may be configured to focus the ultrasound waves onto the body. Layer 720 is the standoff layer and may comprise material including PEBAX. The standoff layer may be formed to make up the difference in height and to level the surface of the acoustic layer. Layer 730 is the acoustic layer and may configured for surface wave modification. Layer 730 may be about 10-100 microns thick with a different speed of sound/ attenuation to reduce acoustic cross talk.

FIG. 7 also shows epoxy layer 740 and heat sink 750. Epoxy layer 740 may comprise an epoxy layer similar to that described in FIG. 5. Heat sink 750 may optionally include heat sink tabs 752. Finally, FIG. 7 shows one or more circuit boards 760 for, among others, power and ultrasound performance management.

The following exemplary embodiments are presented to further illustrate the disclosure principles. Example 1 relates to an ultrasound apparatus, comprising: an ultrasound transducer array, the transducer array having a plurality of CMUTS, each transducer configured to transmit and receive ultrasound signals; an acoustic lens configured over a first surface of the ultrasound transducer array; a circuitry in communication with the ultrasound transducer array, the circuitry to convert the received ultrasound signal to a representative digital signal; and a heat sink configured over a second surface of the transducer array; wherein the acoustic lens includes an outer layer and an inner layer, the outer layer and the inner layer configured to provide at least one of signal attenuation or impedance matching for the transmitted or the received ultrasound signals.

Example 2 relates to the ultrasound apparatus of example 1, wherein the acoustic lens inner layer further comprises a solid mixture of room-temperature vulcanized (RTV) polymer and block polymer.

Example 3 relates to the ultrasound apparatus of example 2, wherein the block polymer is one or more of a thermoplastic material or a block-copolymer.

Example 4 relates to the ultrasound apparatus of example 2, wherein the solid mixture comprises RTV particles dispersed in a block co-polymer.

Example 5 relates to the ultrasound apparatus of example 4, wherein the particles are about 100 microns or less.

Example 6 relates to the ultrasound apparatus of example 2, wherein the RTV polymer comprises one or more of RTV 615 or RTV 630.

Example 7 relates to the ultrasound apparatus of example 1, wherein the solid mixture further comprises a filler.

Example 8 relates to the ultrasound apparatus of example 7, wherein the filler is one or more of $Al_2O_3$ or graphite.

Example 9 is directed to the ultrasound apparatus of example 1, wherein the acoustic lens outer layer comprises RTV 630.

Example 10 is directed to the ultrasound apparatus of example 1, wherein the heat sink further comprises a plurality of tabs.

Example 11 is directed to the ultrasound apparatus of example 1, further comprising a tungsten-epoxy layer interposed between the heatsink and the inner layer of the acoustic lens to attenuate vibration from the transducer.

Example 12 is directed to the ultrasound apparatus of example 11, wherein the tungsten-epoxy layer is integrated into the heat sink.

Example 13 is directed to the ultrasound apparatus of example 1, wherein the outer layer is configured to receive an ultrasound gel pad.

Example 14 relates to an ultrasound apparatus, comprising: an ultrasound transducer array, the transducer array having a plurality of capacitive micromachined ultrasonic transducers (CMUTs), each transducer configured to transmit an ultrasound signal and to receive an ultrasound signal; an acoustic lens configured over a first surface of the ultrasound transducer array; a heat sink positioned over a second surface of the transducer array; a circuit board in communication with the ultrasound transducer array to process the ultrasound signals; wherein the acoustic lens comprises a plurality of signal-attenuating particles in a polymer matrix to thereby provide signal attenuation and impedance matching for the ultrasound signals.

Example 15 is directed to the ultrasound apparatus of example 14, wherein the signal-attenuating particles comprise PEBX.

Example 16 is directed to the ultrasound apparatus of example 14, wherein the polymer matrix comprises a room-temperature vulcanized (RTV) polymer.

Example 17 is directed to the ultrasound apparatus of example 14, wherein the polymer matrix comprises further comprise one or more of $Al_2O_3$ or graphite.

Example 18 is directed the ultrasound apparatus of example 14, wherein the heat sink further comprises a plurality of tabs.

Example 19 is directed to the ultrasound apparatus of example 14, further comprising a tungsten-epoxy layer interposed between the heatsink and the inner layer of the acoustic lens to attenuate transducer vibration.

Example 20 is directed the ultrasound apparatus of example 19, wherein the tungsten-epoxy layer is integrated into the heat sink.

Example 21 is directed to the ultrasound apparatus of example 14, wherein a surface of the acoustic lens is configured to receive an ultrasound gel pad.

Example 22 is directed to the ultrasound apparatus of example 14, wherein the circuit board processes the ultrasound signals by converting a digital signal into an ultrasound signal prior to transmission of the ultrasound signal.

Example 23 is directed to the ultrasound apparatus of example 14, wherein the circuit board processes the ultrasound signal by converting the received ultrasound signal to a digital signal.

Having described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

The techniques described herein are exemplary, and should not be construed as implying any particular limitation on the present disclosure. It should be understood that various alternatives, combinations and modifications could be devised by those skilled in the art from the present disclosure. For example, steps associated with the processes described herein can be performed in any order, unless otherwise specified or dictated by the steps themselves.

What is claimed is:

1. An ultrasound apparatus, comprising:
   an ultrasound transducer array, the transducer array having a plurality of capacitive micromachined ultrasound transducers (CMUTS), each transducer configured to transmit and receive ultrasound signals;
   an acoustic lens configured over a first surface of the ultrasound transducer array;
   a circuitry in communication with the ultrasound transducer array, the circuitry configured to convert the received ultrasound signal to a representative digital signal; and
   a heat sink configured over a second surface of the transducer array;
   wherein the acoustic lens includes an outer layer and an inner layer, the outer layer and the inner layer configured to provide at least one of signal attenuation or impedance matching for the transmitted or the received ultrasound signals; and
   wherein the acoustic lens inner layer further comprises a solid mixture of room-temperature vulcanized (RTV) polymer and block polymer.

2. The ultrasound apparatus of claim 1, wherein the block polymer is one or more of a thermoplastic material or a block-copolymer.

3. The ultrasound apparatus of claim 1, wherein the solid mixture comprises RTV particles dispersed in a block co-polymer.

4. The ultrasound apparatus of claim 3, wherein the particles are about 100 microns or less.

5. The ultrasound apparatus of claim 1, wherein the RTV polymer comprises one or more of RTV 615 or RTV 630.

6. The ultrasound apparatus of claim 1, wherein the solid mixture further comprises a filler.

7. The ultrasound apparatus of claim 6, wherein the filler is one or more of $Al_2O_3$ or graphite.

8. The ultrasound apparatus of claim 1, wherein the acoustic lens outer layer comprises RTV 630.

9. The ultrasound apparatus of claim 1, wherein the heat sink further comprises a plurality of tabs.

10. The ultrasound apparatus of claim 1, further comprising a tungsten-epoxy layer interposed between the heat sink and the inner layer of the acoustic lens to attenuate transducer vibration.

11. The ultrasound apparatus of claim 10, wherein the tungsten-epoxy layer is integrated into the heat sink.

12. The ultrasound apparatus of claim 1, wherein the outer layer is configured to receive an ultrasound gel pad.

13. An ultrasound apparatus, comprising,
    an ultrasound transducer array, the transducer array having a plurality of capacitive micromachined ultrasound transducers (CMUTs), each transducer configured to transmit an ultrasound signal and to receive an ultrasound signal;
    an acoustic lens configured over a first surface of the ultrasound transducer array;
    a heat sink positioned over a second surface of the transducer array;
    a circuit board in communication with the ultrasound transducer array to process the ultrasound signals;
    wherein the acoustic lens comprises a plurality of signal-attenuating particles in a polymer matrix to thereby provide signal attenuation and impedance matching for the ultrasound signals; and
    wherein the signal-attenuating particles comprise PEBAX.

14. The ultrasound apparatus of claim 13, wherein the polymer matrix comprises a room-temperature vulcanized (RTV) polymer.

15. The ultrasound apparatus of claim 13, wherein the polymer matrix further comprises one or more of $Al_2O_3$ or graphite.

16. The ultrasound apparatus of claim 13, wherein the heat sink further comprises a plurality of tabs.

17. The ultrasound apparatus of claim 13, further comprising a tungsten-epoxy layer interposed between the heatsink and an inner layer of the acoustic lens to attenuate transducer vibration.

18. The ultrasound apparatus of claim 17, wherein the tungsten-epoxy layer is integrated into the heat sink.

19. The ultrasound apparatus of claim 13, wherein a surface of the acoustic lens is configured to receive an ultrasound gel pad.

20. The ultrasound apparatus of claim 13, wherein the circuit board processes the ultrasound signals by converting a digital signal into an ultrasound signal prior to transmission of the ultrasound signal.

21. The ultrasound apparatus of claim 13, wherein the circuit board processes ultrasound signals received by the transducer array by converting them to digital signals.

* * * * *